United States Patent [19]

Fritzberg et al.

[11] Patent Number: 5,322,929

[45] Date of Patent: Jun. 21, 1994

[54] RADIOLABELED TECHNETIUM CHELATES FOR USE IN RENAL FUNCTION DETERMINATIONS

[75] Inventors: Alan Fritzberg, Edmonds; Sudhaker Kasina, Kirkland, both of Wash.; Dennis L. Johnson, Las Cruces

[73] Assignee: University of Utah Research Foundation, Salt Lake City, Utah

[21] Appl. No.: 389,188

[22] Filed: Aug. 3, 1989

Related U.S. Application Data

[63] Continuation of Ser. No. 733,481, May 14, 1985, Pat. No. 4,980,147, which is a continuation-in-part of Ser. No. 624,098, Jun. 24, 1984, abandoned.

[51] Int. Cl.[5] .......................... C07K 5/08; C07K 5/10
[52] U.S. Cl. ........................................ 530/330; 530/331
[58] Field of Search ............... 534/10, 14; 424/1.1; 530/300, 331, 330; 514/2, 18; 930/22, 24, 30

[56] References Cited

U.S. PATENT DOCUMENTS 3,822,509  9/1974  Brown et al. ............... 252/301.1 R
3,830,746  8/1974  Brown ........................... 252/301.1 B (List continued on next page.)

FOREIGN PATENT DOCUMENTS 173424  3/1986  European Pat. Off. .............. 534/14

OTHER PUBLICATIONS

Chem. Abs. 69 (23), 97137k, Nakahara et al. (1968) "Reactions of Metal Chelates . . . ".
Chem. Abs. 86 (23) 171827e, Yamane et al. (Jun. 6, 1977) "Decarboxylation reaction . . . ".

(List continued on next page.)

*Primary Examiner*—Robert L. Stoll
*Assistant Examiner*—John M. Covert
*Attorney, Agent, or Firm*—Workman, Nydegger & Jensen

[57] ABSTRACT

The present invention is directed to novel radiopharmaceutical imaging agents incorporating Tc-99m as a radiolabel. In particular, the novel imaging agents disclosed herein have relatively high renal extraction efficiencies, and hence are useful for conducting renal function imaging procedures. The novel Tc-99m compounds of a present invention have the following general formula:

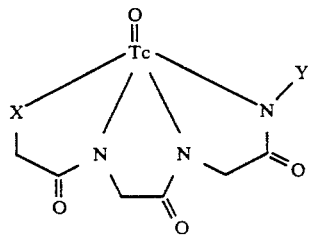

wherein X is S or N; and wherein Y is —H or wherein Y is

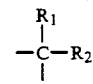

and where $R_1$ is —H, —CH$_3$, or —CH$_2$CH$_3$; $R_2$ is —H, —CH$_2$CO$_2$H, —CH$_2$CONH$_2$, —CH$_2$CH$_2$CO$_2$H, —CH$_2$CH$_2$CONH$_2$, —CH$_3$, —CH$_2$CH$_3$, CH$_2$C$_6$H$_5$, or —CH$_2$OH; and Z is —H, —CO$_2$H, —CONH$_2$, —SO$_3$H, —SO$_2$NH$_2$, or —CONHCH$_2$CO$_2$H; and the Tc is Tc-99m; and water-soluble salts thereof. Of the foregoing, the presently preferred Tc-99m compound of the present invention is Tc-99m-mercaptoacetylglycylglycylglycine (Tc-99m-MAGGG). The present invention is also directed to novel chelating agents that may be reacted with Tc-99m to form the foregoing compounds. Such novel chelating agents have the following general formula.

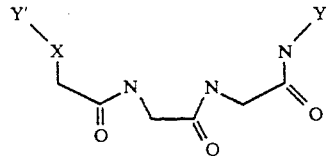

where X and Y have the same definitions as above, and wherein Y' is —H$_2$ when X is N, or wherein Y' is —H, or a suitable protective group such as —COCH$_3$, —COC$_6$H$_5$, —CH$_2$NHCOCH$_3$, —COCF$_3$, or —COCH$_2$OH when X is S. The present invention also provides methods for preparing and using the novel Tc-99m compounds.

7 Claims, 1 Drawing Sheet

U.S. PATENT DOCUMENTS

| | | | |
|---|---|---|---|
| 3,912,935 | 10/1975 | Harris | 250/506 |
| 4,048,296 | 9/1977 | Wolfangel | 424/1.1 |
| 4,296,785 | 10/1981 | Vittello et al. | 141/105 |
| 4,434,151 | 2/1984 | Byrne et al. | 424/1.1 |
| 4,444,690 | 4/1984 | Fitzberg | 424/1.1 X |
| 4,615,876 | 10/1986 | Troutner et al. | 424/1.1 |
| 4,670,545 | 6/1987 | Fitzberg et al. | 534/14 |
| 4,849,511 | 7/1989 | Verbruggen | 534/14 |
| 4,861,869 | 8/1989 | Nicolotti et al. | 424/1.1 X |
| 4,883,862 | 11/1989 | Chervu et al. | 424/1.1 X |
| 4,925,650 | 5/1990 | Nosco et al. | 424/1.1 |
| 4,965,392 | 10/1990 | Fritzberg et al. | 424/1.1 X |
| 4,980,147 | 12/1990 | Fritzberg et al. | 424/1.1 |

OTHER PUBLICATIONS

Chem. Abs. 90 (22) 179658d, H. A. Sokol, (May 28, 1979) "Detection of N-acetylglycylglycine . . . ".

Chem. Abs. 97 (23) 196268p, Adibi et al. (Dec. 6, 1982) "Enrichment of glycine pool in plasma . . . ".

Chem. Abs., vol. 61, No. 6, Abs. #8395e, Sep. 1964.

Chem. Abs., vol. 90, No. 23, Abs #187323f, Jun. 1979.

Sugiura, Inorganic Chemistry, vol. 17, No. 8, pp. 2176-2182, 1978.

Chem. Abs., vol. 70, No. 15, abs. 68727t (1969).

Simic et al., *Radiation Research*, vol. 48, pp. 244-255 (1971).

Brubacher et al., *Biochem. Biophys Res. Comm.*, vol. 27, No. 2, pp. 176-182 (1967).

Dorigatti et al., *J. Inorg. Nucl. Chem.*, vol. 37, pp. 1515-1520 (1975).

Sugiura, Yokio; "Newly Synthesized Sulfhydryl- and Imidazole-Containing Tripeptides with a Specific Copper-Binding Site"; Faculty of Pharmaceutic, Kyoto University, Kyoto.

W. C. Klingensmith III, et al., "Clinical Comparison of Tc-99m N,N'-Bis (mercaptoacetamido) ethylenediamine and ([131]) ortho-iodohippurate for Evaluation of Renal Tubular Function: Concise Communication" The Journal of Nuclear Medicine, May 1982, vol. 23, No. 5, pp. 377-380.

Alan R. Fritzberg, et al., "Synthesis and Biological Evaluation of Tc-99m N,N'-Bis(mercaptoacetyl)-2, 3-diaminopropanoate: A Potential Replacement for ([131])-iodohippurate" The Journal of Nuclear Medicine, Jul. 1982, vol. 23, No. 7.

Mallinckrodt, Inc., Technical Product Data, "HIPPURAN R I 131 INJECTION Iodohippurate Sodium I 131 Injection Diagnostic-For Intravenous Use", R1/83 MK-20348 (Mallinckrodt Inc., Diagnostic Products Division, St. Louis, MO (63134).

W. C. Klingensmith III, et al., "Clinical Evaluation of Tc-99m N,N'-Bis (mercaptoacetyl)-2, 3-Diaminopropanoate as a Replacement for I-131 Hippurate: Concise Communication", The Journal of Nuclear Medicine, vol. 25, No. 1.

R. F. Schneider, et al., "N,N'-bis(S-Benzoylmercaptoacetamido) Ethylenediamine and Propylenediamine Ligands as Renal Function Imaging Agents. 1. Alternate Synthetic Methods" The Journal of Nuclear Medicine, vol. 25, No. 2.

Richard F. Schneider, "Alternate Synthesis and Evaluation of a Series of N,N-Bis(Mercaptoacetamido) Ethylenediamine and Propylenediamine Ligands as Renal Imaging Agents," Division of Nuclear Medicine; The Upstate Medical Center, 750 E. Adams Street, Syracuse, New York 13210.

A. Fritzberg, et al., "A Potential Tc-99m Renal Tubular Function Agent: Tc-99m-BIX-N.N'-(MERCAPTOACETAMIDO)-2,3-DIAMINOPROPONOATE".

A. R. Fritzberg et al., "Synthesis and Evaluation of $N_2S_2$ Complexes of Tc-99m as Renal Function Agents," The Journal of Nuclear Medicine, vol. 25, p. 16 (May 1984).

Alan R. Fritzberg, "Current Status of Renal Radiopharmaceuticals," Journal of Nuclear Medicine Technology, vol. 12, No. 4, pp. 177-188 (Dec. 1984).

Fritzberg, Alan et al., "Synthesis and Biological Evaluation of Technetium-99 $MAG_3$ as a Hippuran Replacement," *Journal of Nuclear Medicine*, 27:1, pp. 111-116 (Jan. 1986).

Kasina, Sudhakar et al., "Tissue Distribution Properties of Technetium-99m-Diamide-Dimercaptide Complexes and Potential Use of Renal Radiopharmaceuticals," *Journal of Medicinal Chemistry*, 29, pp. 1933-1940 (1986).

(List continued on next page.)

OTHER PUBLICATIONS

A. Verbruggen, et al., "Evaluation of the Diastereomers of Tc-99m-Mercaptoace-Tylglycyl-D-Alanylglycine (Tc-99m-D-Magag) in Primates," *The Journal of Nuclear Medicine*, vol. 29. No. 5, May 1988.

Verbruggen, A., et al., "Evaluation of the Renal Excretion Characteristics of Tc-99m–Mercaptoacetylglycyl-D-Serylglycine," *The Journal of Nuclear Medicine*, vol. 28, No. 4, Apr. 1987.

Nosco, D., et al. "Preparation and Evaluation of $MAG_3$-Like Compounds as Renal Agents", *The Journal of Nuclear Medicine*, vol. 30, No. 5, May, 1989.

Nosco, D., et al, "Chemistry of Tc-$MAG_3$ and Derivatives; Synthesis, Characterization, Reactivity and Biodistribution of these Complexes", *The Journal of Nuclear Medicine*, vol. 29, No. 5, May, 1988.

RADIOLABELED TECHNETIUM CHELATES FOR USE IN RENAL FUNCTION DETERMINATIONS

PRIOR APPLICATIONS

This is a continuation application under 37 C.F.R. § 1.60, of pending prior application Ser. No. 06/733,481 filed on May 14, 1985, of Alan Fritzberg, Sudhakar Kasina and Dennis L. Johnson for RADIOLABELED TECHNETIUM CHELATES FOR USE IN RENAL FUNCTION DETERMINATIONS, now issued as U.S. Pat. No. 4,980,147, which is a continuation-in-part of Ser. No. 06/624,098 filed on Jun. 24, 1984, now abandoned.

BACKGROUND

1. The Field of the Invention

The present invention is related to methods and compounds for use in the field of determining renal function by means of scintigraphic urography. More particularly, the present invention is directed to renal system imaging in which technetium-99m radiolabeled chelates are used.

2. The Prior Art

Regulation of the content and quantity of body fluids is critical to the basic physiology of bodily functions. For instance, it is necessary for the body to regulate such fluid-related variables as total body fluid volume, constituents of extracellular body fluids, the acid-base balance in body fluids, and various factors that affect interchange of extracellular and intracellular fluids (most notably, factors that affect the osmotic relationship between such fluids).

The kidneys are the primary body organs that are responsible for regulation of the composition of body fluids. Thus, the kidneys maintain body fluids within a physiologically acceptable range by excreting most of the end products of metabolism and by regulating the concentrations of desirable body fluid constituents.

The human body contains two kidneys that function to form urine containing fluid constituents that are to be eliminated through the bladder. The basic biological unit that performs the work of the kidney is the "nephron." Each kidney is comprised of some one million nephrons, with each nephron being capable of regulating body fluid independently of other nephrons.

The kidneys function on body fluid by filtering a substantial volume of blood (about one-fifth of the total cardiac output is pumped directly to the kidneys); this specific volume of blood is known as the "renal fraction." Blood flow through the kidneys of a typical adult male averages about 1.2 liters per minute. As the blood passes through the kidneys, the nephrons "clear" the blood plasma of unwanted substances—for example, the metabolic end products (such as urea, creatinine, uric acid, sulfates and phenols) and the nonmetabolic ionic substances (such as excess sodium, potassium, and chloride).

The nephrons are basically comprised of a capillary bed termed the "glomerulus," a second capillary bed known as the "peritubular" capillaries, and a urine-forming component known as the "tubule." The tubule is separated from the glomerulus by a membrane known as the "glomerular membrane." As the renal fraction of blood flows through the glomerulus, the glomerular membrane passes a small proportion (generally no more than 20%-25%) of the plasma comprising the renal fraction into the tubule. This filtered fluid then flows through the tubule, and towards the pelvis of the kidney, which in turn feeds into the bladder. As fluids flows through the tubule, most of the water and much of the electrolytes and other "wanted" substances are reabsorbed and returned to the blood; the "unwanted" substances (such as metabolic end products and excess water and electrolytes) pass into the bladder for elimination as urine.

The remaining portion of the renal fraction that does not cross the glomerular membrane exits the glomerulus and then enters the peritubular capillaries; from there, a portion of the renal fraction is generally returned to the venous system. The large quantities of fluid components reabsorbed in the tubules are also transported to the peritubular capillaries by diffusion through the tubular membrane.

While large quantities of fluid diffuse from the tubule into the peritubular capillaries for return to the vascular system, diffusion of some plasma components occurs in the reverse direction—from the peritubular capillaries to the tubules. For instance, sodium ions are actively transported across the tubular membrane and into the peritubular fluid, thereby conserving this important electrolyte. However, this creates a substantial negative charge within the tubule with respect to the peritubular fluid. In the proximal tubule, this electrical difference is approximately 20 millivolts, and can climb to as much as 120 millivolts in the distal tubule.

This difference in electrical potential potentiates diffusion of some positive ions, most notably potassium, from the peritubular fluid into the tubule. This flow of potassium into the tubules across the tubular membrane due to the electronegativity gradient is termed "passive secretion."

In addition to this passive secretion, some ionic materials are "actively" secreted into the tubules. For instance, para-aminohippuric acid (generally referred to as "PAH") is actively secreted from the peritubular fluid into the tubules; although only about twenty percent (20%) of the renal fraction passes into the tubules as glomerular filtrate, nearly ninety percent (90%) of any PAH in the blood is removed by the kidneys. Thus, approximately seventy percent (70%) of the PAH is removed from the plasma by active secretion into the tubules.

Occasionally, a kidney will become damaged and thus diminish or even cease its function of clearing the blood. Various renal function tests have been devised to assist a physician to evaluate the extent and type of kidney damage that has occurred. Also, these renal function tests are useful in evaluating whether a kidney is operating properly following a kidney transplant operation.

One such renal function testing procedure is known as intravenous scintigraphic urography (this procedure is also commonly known as a dynamic renal function imaging study). This procedure has historically involved the intravenous administration of a radioactively labeled iodine substance, such as I-131 ortho-iodohippurate (often referred to as "I-131 OIH"). Like PAH, I-131 OIH is rapidly removed from the blood by active tubular secretion in addition to glomerular filtration, thereby causing significant quantities of radiolabeled material to concentrate in the kidneys within a few minutes after administration. Images can be obtained using gamma scintillation cameras capable of showing the location of this radiolabeled material, and thereby giving a useful indication of the quality of renal function in the kidneys.

Despite the fact that I-131 OIH is an important tool in evaluating renal function, it suffers from some significant drawbacks. First, because of the high-energy gamma radiation output (364 KeV) of iodine-131 ("I-131"), the use of I-131 OIH results in images having poor spatial resolution. This makes it difficult to observe fine detail within the kidneys, and thereby limits the amount of useful information which is obtainable by this method.

Further, the renal extraction efficiency (the ability to clear the radiopharmaceutical from blood passing through the kidneys) of I-131 OIH is only about 65%–80%, and, while this is quite good, a higher extraction efficiency would result in higher kidney-to-background ratios, which facilitate detection of minimal renal function. In addition, I-131 emits a beta particle during radioactive decay which can cause damage to surrounding tissue. Further, because free radioiodine that accompanies I-131 OIH is readily taken up by the patient's thyroid gland, the maximum dose of I-131 OIH must generally be held to about 200 to 300 microcuries. This low dosage requires a significant exposure period when taking the radioactive image, which in turn decreases the temporal resolution of sequential images taken during renal function studies.

In order to improve upon the resolution obtainable in a radioactive renal function procedure, alternative radiolabeled materials have been earnestly sought. It is currently believed that the most desirable radioactive label is technetium-99m ("Tc-99m"), which has significantly improved resolution properties when compared to the I-131 label, because Tc-99m emits a lower energy (140 KeV) radiation. This lower energy radiation is well-suited for use in connection with standard radiation-measuring instrumentation. The radiation dose per millicurie is much less for Tc-99m than is the case when using I-131; this is because Tc-99m has a half-life of only about six (6) hours (as opposed to a half-life of eight (8) days for I-131), and also because Tc-99m does not emit beta particles during its decay process.

The radioactive properties of Tc-99m result from the transition of the metastable excited nucleus to ground state Tc-99. The resulting Tc-99 has such a long half-life (200,000 years) as to be virtually innocuous. As a result, dosages of as much as 30,000 microcuries of Tc-99m may be administered without danger to the patient. The result is that much shorter exposure periods are required than when I-131 OIH is used. This in turn makes it possible to take acceptable perfusion images during the first pass of radiopharmaceutical through the kidneys.

The foregoing properties of Tc-99m make it ideal as a tool in nuclear medicine, since it is well-suited for use with standard instrumentation, and because it subjects the patient with whom it is used to a relatively low dose of radiation.

Because of the demonstrated advantages of the Tc-99m label over the I-131 label, a great deal of effort has gone into developing a Tc-99m compound having a high renal extraction efficiency. A number of Tc-99m-labeled chelates have been reported in the literature.

One Tc-99m-labeled compound, Tc-99m diethylenetriaminepentaacetic acid (generally referred to as "Tc-99m-DTPA") has sometimes been used in radioactive renal function evaluation procedures because of its excellent imaging characteristics. However, Tc-99m-DTPA is not actively secreted into the tubules of the kidney, and thus has a maximum extraction efficiency of only about 20–25%; this would be expected in connection with a substance entering the tubules only as a result of glomerular filtration. This lower extraction efficiency makes the use of Tc-99m-DTPA less sensitive in detecting mild renal disease than is I-131 OIH. Even so, because of the ability of Tc-99m-DTPA to provide perfusion images of the renal blood supply to the kidneys during the first pass after injection, it is common to use Tc-99m-DTPA together with I-131 OIH.

Another Tc-99m compound reported in the literature is Tc-99m-N,N'-bis (mercaptoacetyl)-ethylenediamine ("Tc-99m-DADS"). While this compound has been found to be secreted in the tubules, the tubular extraction efficiency of Tc-99M-DADS is only about 53% in normal patients, and even less in patients having decreased renal function. This very low extraction efficiency makes this compound unsuitable as a replacement for I-131 OIH.

Although Tc-99m-DADS is itself deemed unsatisfactory as a replacement for I-131 OIH, the fact that it is actively secreted by the tubules led to experimentation with various analogs. For instance, various methyl, hydroxymethylene, benzo, carboxylate, dicarboxylate, and benzocarboxylate analogs have been synthesized and tested.

Of these, the most efficiently excreted analog has been Tc-99m-N,N'-bis (mercaptoacetyl)-2,3-diaminopropanoate (Tc-99mCO$_2$-DADS). Unfortunately, this ligand exists as two stereoisomeric products upon chelation, referred to as Tc-99m-CO$_2$-DADS-A and Tc-99m-CO$_2$-DADS-B. Further, the Tc-99m-CO$_2$-DADS-B isomer was found to be far less efficiently removed by the kidneys than was the Tc-99m-CO$_2$-DADS-A isomer. Because of the inherent difficulty in separating these two isomers for clinical use, commercial development of Tc-99m-CO$_2$-DADS-A has proven to be impractical.

From the foregoing, it will be appreciated that it would be a substantial improvement in the field of renal function imaging if a Tc-99m compound could be provided that has a relatively high extraction efficiency, yet does not exhibit other adverse properties that would make it unsuitable as a replacement for I-131 OIH. Because of the short half-life of Tc-99m, it would also be a significant advancement if such Tc-99m imaging compounds could be easily prepared immediately prior to conducting a renal function diagnostic procedure. Such Tc-99m compounds and methods are disclosed and claimed herein.

BRIEF SUMMARY AND OBJECTS OF THE INVENTION

The present invention is directed to novel radiopharmaceutical imaging agents incorporating Tc-99m as a radiolabel. In particular, the novel imaging agents disclosed herein have relatively high renal extraction efficiencies, and hence are useful for conducting renal function imaging procedures. The novel Tc-99m compounds of the present invention are believed to have the following general formula:

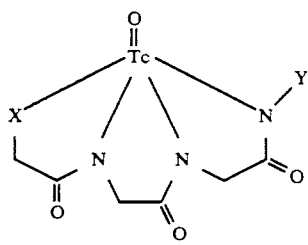

wherein X is S or N; and wherein Y is —H or wherein Y is

and wherein $R_1$ is —H, —CH$_3$, or —CH$_2$CH$_3$; $R_2$ is —H, —CH$_2$CO$_2$H, —CH$_2$CONH$_2$, —CH$_2$CH$_2$CO$_2$H, —CH$_2$CH$_2$CONH$_2$, —CH$_3$, —CH$_2$CH$_3$, or —CH$_2$OH; and Z is —H, —CO$_2$H, —CONH$_2$, —SO$_3$H, —SO$_2$NH$_2$, or —CONHCH$_2$CO$_2$H; and wherein Tc is Tc-99m; and water-soluble salts thereof.

Of the foregoing, a presently preferred Tc-99m compound of the present invention is Tc-99m-mercaptoacetylglycylglycylglycine (Tc-99m-MAGGG). Other presently preferred compounds are Tc-99m-MAGG-Alanine, Tc-99m-MAGG-Glutamine, and Tc-99m-MAGG-Asparagine.

The present invention is also directed to novel chelating agents that may be reacted with Tc-99m to form the foregoing compounds. Such novel chelating agents have the following general formula:

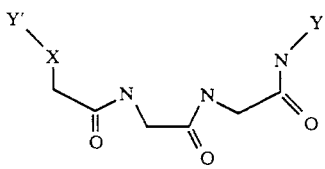

where X and Y have the same definitions as above, and wherein Y' is —H$_2$ when X is N, or wherein Y' is —H, —COCH$_3$, —COC$_6$H$_5$ or —CH$_2$NHCOCH$_3$, —COCH$_2$OH, —COCH$_2$CO$_2$H or other suitable protective group when X is S.

The present invention also provides methods for preparing and using the novel Tc-99m compounds.

It is, therefore, a principal object of the present invention to provide novel Tc-99m compounds useful in scintigraphic procedures.

A further object of the present invention is to provide novel Tc-99m compounds that are rapidly and efficiently cleared by the kidneys so as to be useful in the field of renal function imaging.

Yet a further object of the present invention is to provide methods for preparing Tc-99m compounds immediately prior to their use as an imaging agent.

Still another object of the present invention is to provide methods for evaluating renal function using novel Tc-99m compounds.

These, and other compounds and features of the present invention, will become more fully apparent from the following description and appended claims taken in conjunction with the accompanying drawing.

DETAILED DESCRIPTION OF THE INVENTION

Figure 1:
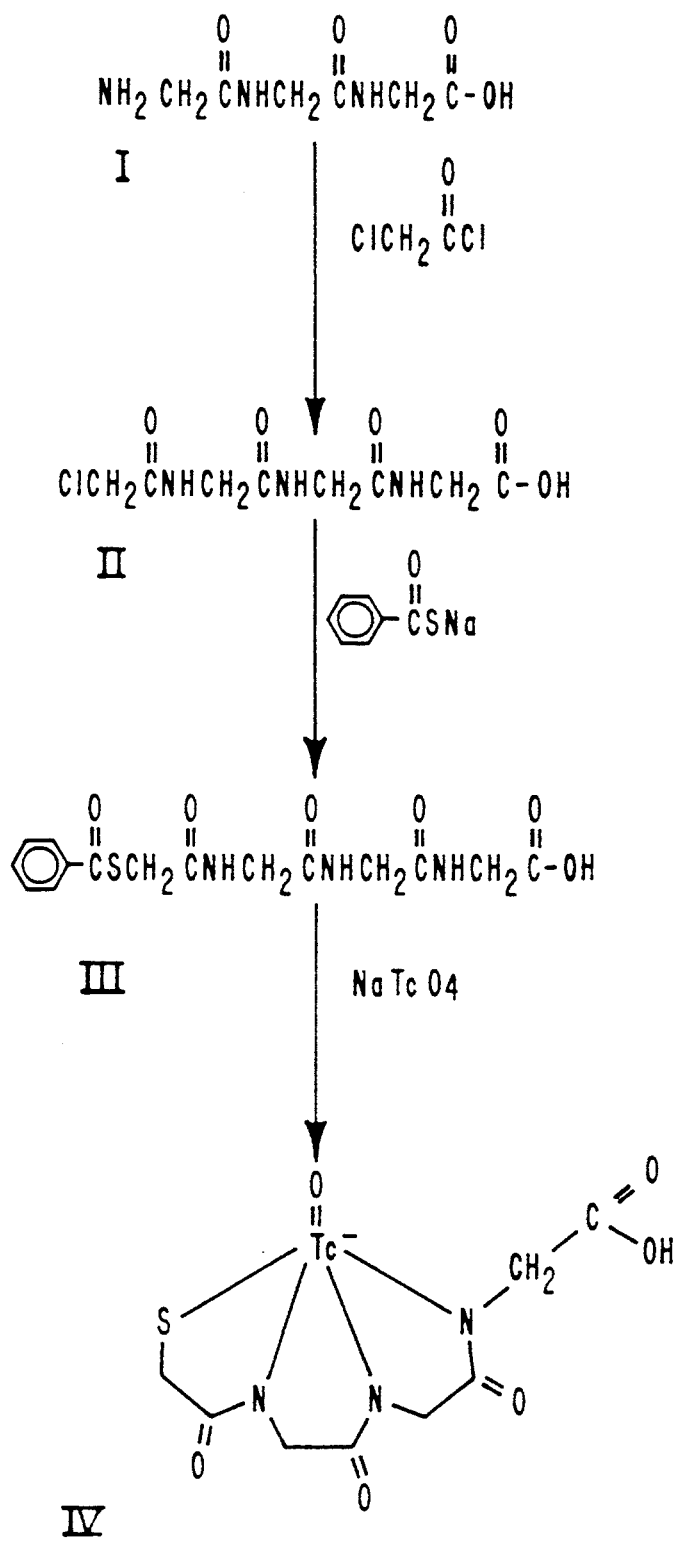
FIG. 1 is a diagram illustrating a presently preferred process for synthesizing Tc-99m-MAGGG, a compound within the scope of the present invention.

The present invention is directed to novel Tc-99m compounds that are actively secreted into the tubules of the kidneys, and thus are excellent candidates for use in renal function tests, such as radioactive urography procedures.

More particularly, the present invention is directed to Tc-99m-mercaptoacetyl-tri-amino acid compounds (an N$_3$S system), and especially Tc-99m-mercaptoacetyl-glycylglycylamino acid compounds having the general formula:

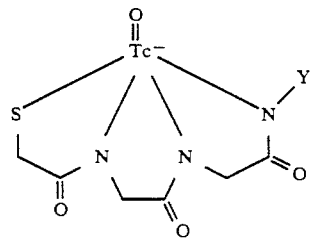

where Y is —H or where Y is:

and where $R_1$ is —H, —CH$_3$, or —CH$_2$CH$_3$; $R_2$ is —H, —CH$_2$CO$_2$H, —CH$_2$CONH$_2$, —CH$_2$CH$_2$CO$_2$H, —CH$_2$CH$_2$CONH$_2$, —CH$_3$, —CH$_2$CH$_3$, or —CH$_2$OH; and Z is —H, —CO$_2$H, —CONH$_2$, —SO$_3$H, —SO$_2$NH$_2$, or —CONHCH$_2$CO$_2$H.

The present invention also includes Tc-99m compounds similar to the general formula set forth above, except that the sulfur is replaced by nitrogen (an N$_4$ system) as set forth below:

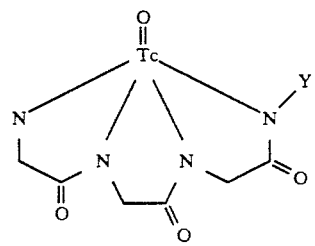

where Y has the same definition as above.

In addition to the foregoing, the present invention is directed to Tc-99m compounds having the following general structure:

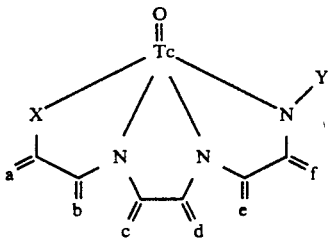

where X is S or N; where Y has the same definition as above; and wherein each small letter a–f represents either 2 hydrogens or a double-bonded oxygen: where X is S, then element a represents two hydrogens and at least two of elements b–f are double-bonded oxygens, and the remaining elements are two hydrogens; where X is N, then at least two of elements a–f are double-bonded oxygens, and the remaining elements are two hydrogens.

In addition to each of the compounds illustrated above, the present invention includes the water-soluble salts thereof.

The present invention also includes novel chelating agents that may be reacted with Tc-99m to form the foregoing compounds. Such novel chelating agents have the following general formula:

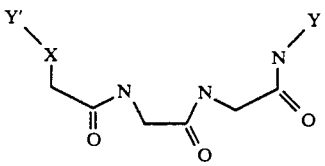

where X and Y have the same definitions as above, and wherein Y' is —$H_2$ when X is N, or wherein Y' is —H, —COCH$_3$, —COC$_6$H$_5$, —CH$_2$NHCOCH$_3$, —COCH$_2$OH, —COCH$_2$CO$_2$H or other suitable protective group when X is S. When X is S and Y' is one of the foregoing groups other than —H, the use of Y' serves to protect the sulfur from oxidation. No such protection is necessary when X is N.

The presently preferred process for synthesizing the novel Tc-99m compounds of the present invention is set forth in FIG. 1, wherein is specifically illustrated the process for synthesizing Tc-99m-mercaptoacetylglycylglycylglycine (Tc-99m-MAGGG).

Thus, in FIG. 1, it is seen that glycylglycylglycine (Compound I) is reacted with chloroacetyl chloride in order to produce chloroacetylglycylglycylglycine (Compound II). Compound II is next reacted with sodium thiobenzoate in order to form benzoyl mercaptoacetylglycylglycylglycine (Compound III). Compound II is finally reacted with sodium pertechnetate in the presence of a suitable reducing agent so as to produce Tc-99m-MAGGG (Compound IV). It will be appreciated that the same general synthesis pathway may be used with other starting ligands in order to produce other Tc-99m compounds within the scope of the present invention.

The novel Tc-99m compounds of the present invention are used in scintigraphic urography procedures by administration thereof to a patient by intravenous injection, followed by recording of images of the patient's kidneys by means of gamma scintillation cameras. As mentioned above, it is possible to administer dosages of as much as 30,000 microcuries of Tc-99m; this is extremely beneficial in conducting dynamic tests of renal function because of the short exposure periods that are possible with such a high dosage.

It has been found that the novel Tc-99m compounds of the present invention are actively secreted into the tubules of the kidneys, thereby providing significantly high extraction deficiencies so that they are capable of serving as substitutes for I-131 OIH. Additionally, it will be appreciated from an examination of the structures set forth above that the novel compounds do not exist in stereo-isomeric forms that might make practical applications more difficult (although diasteriomeric forms can exist dependent upon the choice of the Y group).

As mentioned above, Tc-99m has a half-life of only about six (6) hours. Because of this short half-life, it is not practical to package a Tc-99m-chelate ready for clinical use. An important feature of the present invention is the ability to package the reagents in a kit form that permits easy preparation of the Tc-99m-chelate immediately prior to use as a radiopharmaceutical.

Thus, although in the laboratory it has been found practical to react mercaptoacetylglycylglycylglycine with Tc-99m pertechnetate in the presence of the reducing agent dithionite, both the Tc-99m and the dithionite must be freshly prepared.

A more conveniently synthesis process has been discovered using stannous ion complexed with a suitable intermediate exchange ligand such as acetate, tartrate, malate, lactate, hydroxyisobutyrate, citrate, glucoheptonate, gluconate, pyrophosphate, N-methyl N,N'-bis (2-hydroxyethyl)ethylenediamine, or glycine. It has been found that the stannous ion is capable of inducing the reaction of a ligand such as that of Compound III of FIG. 1 with sodium pertechnetate to form a Tc-99m compound such as Compound IV of FIG. 1.

The stannous ion is not unstable in solution as is dithionite; hence, the process utilizing stannous ion is readily susceptible for packaging in a kit form, consisting of two parts, the stannous ion (and intermediate exchange ligand) and ligand to be attached to the Tc-99m being provided in one vial, capable of long-term storage, and sodium pertechnetate in another vial. Generally, the sodium pertechnetate will be locally prepared from readily available Mo-79/Tc-99m generators because of the short half-life of Tc-99m.

A few representative examples will assist in the understanding of the present invention. Examples I and II describe a presently preferred process for synthesizing mercaptoacetylglycylglycylglycine and Tc-99m-MAGGG, respectively.

EXAMPLE 1

Synthesis of a Benzoyl Mercaptoacetylglycylglycylglycine

The synthesis of benzoyl mercaptoacetylglycylglycylglycine was accomplished as a multi-step process beginning with dissolving 2.5 grams of glycylglycylglycine in 75 millimeters of 1.0 Normal sodium hydroxide in a 500 milliliter flask at 0° C. and under a nitrogen atmosphere.

A solution of 13.0 grams of chloroacetyl chloride in 100 milliliters of ether was then added dropwise from one addition funnel, while 100 milliliters of 1.0 Normal sodium hydroxide was simultaneously added dropwise from a second addition funnel, at the same time continuously stirring the glycylglycylglycine solution. Following dropwise addition of the chloroacetyl chloride and sodium hydroxide, the reaction mixture was maintained at 0° C. while being stirred for an additional 1.5 hours.

Next, the reaction mixture was acidified to a pH of about 2 by addition of concentrated hydrochloric acid. After stirring for yet an additional 30 minutes, the reaction mixture was warmed to 40° C. and concentrated to one-third of its volume under reduced pressure.

The concentrated mixture was then cooled in an ice bath in order to precipitate out chloroacetylglycylglycylglycine; after two washings with water, it was found that 2.75 grams of chloroacetylglycylglycylglycine was obtained, a yield of 78.5% in the amount of glycylglycylglycine dissolved in the starting mixture.

One gram of the crude chloroacetylglycylglycylglycine was next dissolved in 300 milliliters of anhydrous methanol under a nitrogen atmosphere. Fifty (50) milliliters of a solution containing sodium thiobenzoate (prepared from 175 milligrams of sodium in methanol to which 1.1 gram of thiobenzoic acid was added) was then added to the flask, and the reaction mixture was refluxed for 1.5 hours.

Next, the solvent was removed under reduced pressure. The resultant solid was isolated by filtration and washed with chloroform. Crystallization from methanol resulted in recovery of 1.25 grams (90%) of benzoyl mercaptoacetylglycylglycylglycine.

An elemental analysis was conducted to verify that benzoyl mercaptoacetylglycylglycylglycine was the product obtained from crystallization from methanol. The calculated theoretical percentages of carbon, hydrogen, nitrogen, and sulfur comprising benzoyl mercaptoacetylglycylglycylglycine are 56.56, 4.92, and 5.74, and 13.11, respectively. The results of the elemental analysis were 56.50, 5.06, 5.67, and 13.27, respectively. The substantial agreement between the theoretical and experimental analyses clearly indicates that the product of this reaction sequence was benzoyl mercaptoacetylglycylglycylglycine.

EXAMPLE 2

Synthesis of Tc-99m Mercaptoacetylglycylglycylglycine

As mentioned above, one important feature of the present invention is the ability to package precursors to the desired imaging agent in a kit form. This example describes the preparation of such a "kit" in the contexts of Tc-99m-MAGGG as an imaging agent.

For instance, in preparing about 100 "kits," 80 milliliters of 1.25 Molar intermediated exchange ligand (e.g., acetate, glycine, citrate, malonate, gluconate, glucoheptonate, pyrophosphate, tartrate, malate, lactate, hydroxyisobutyrate, or N-methyl N, N'-bis (2-hydroxyethyl) ethylenediamine) is adjusted to a pH of about 5.5 and then deoxygenated by purging with nitrogen gas. One hundred milligrams of benzoyl mercaptoacetylglycylglycylglycine is then added with stirring until a clear solution is obtained.

Next, 0.20 milliliters of a freshly prepared 10.0 milligrams/milliliters solution of $SnCl_2.2H_2O$ in 1 milliliter of 0.1 Normal hydrochloric acid is added to the mixture under a nitrogen atmosphere. Finally, the pH of the resulting mixture is adjusted to about 5 by addition of appropriate amounts of 0.1 Normal HCl or NaOH, diluted to 100 milliliters total volume, and the solution is sterilized by passage through a 0.2 micron filter, while still maintaining a nitrogen atmosphere. Finally, 1.0 milliliter aliquots are dispensed into vials using a sterile technique, and the individual aliquots are frozen or freeze dried for storage. Optionally, a stannous ion stabilizer (such as gentisic acid or ascorbic acid) is also added.

A volume of about 1 to 3 milliliters of Tc-99m pertechnetate in saline having the desired level of radioactivity (as high as 50 millicuries per milliliter is acceptable) is obtained from a Mo-99/Tc-99m generator and added to one of the vials containing reactants prepared as set forth above. After mixing, the vial is placed into a boiling water bath for five minutes in order to effect the reaction which results in formation of Tc-99m-MAGGG. Upon cooling, the preparation may be used with no further treatment.

EXAMPLE 3

Analysis Procedures

Where desired, routine analysis of Tc-99m-MAGGG is advantageously conducted by use of thin layer chromatography on ITLC-SG silica gel impregnated glass fiber strips, such as those obtainable from Gelman, Inc., Ann Arbor, Mich.

The amount of soluble, unbound Tc-99m pertechnetate is determined by the radioactivity at the solvent front of a strip developed in methylethyl ketone. The amount of insoluble Tc-99m is obtained by measuring the radioactivity from the fraction at the origin on a strip developed in saline. The percentage of bound Tc-99m is calculated according to the following formula:

$$\% \ bound = 100 - \% \ unbound - \% \ insoluble$$

An analysis of the chelated Tc-99m-MAGGG product may be conducted through use of high performance liquid chromatography ("HPLC") using a 5 micron ODS column with a solvent system comprising 5% ethanol:95% 0.01 Molar phosphate at a pH of 6. Tc-99m-MAGGG is the major peak at about 4 minutes when using a 1.0 milliliter per minute flow rate. Other components that may be observed are Tc-99m pertechnetate at about 2.5 minutes.

EXAMPLE 4

Renal Uptake of Tc-99m-MAGGG in Normal Mice

Tc-99m-MAGGG was administered simultaneously with I-131 OIH (as a reference standard) to size mice in two groups. Each mouse was injected intravenously with 0.1 milliliters of a preparation containing 0.5 microcuries of Tc-99m-MAGGG and 0.2 microcuries of I-131 OIH, and then placed into a metabolic cage capable of collecting excreted urine.

Ten minutes after injection, each mouse's urethra was ligated and the mouse was sacrificed by chloroform vapor; various samples were then taken to determine biodistribution of radiolabeled material. The results of these samples are shown in Table I. Similar measurements, shown in Table II, were taken on the second group of mice 120 minutes after injection.

TABLE I

BIODISTRIBUTION IN NORMAL MICE AFTER 10 MINUTES
(Numbers expressed as percentage of radioactive agent initially injected)

| Agent | Blood | Liver | Kidneys | Stomach | Intestine | Urine |
|---|---|---|---|---|---|---|
| Tc-99m-MAGGG | 2.6 | 2.9 | 3.5 | 0.1 | 1.1 | 79.9 |
| I-131 OIH | 4.1 | 1.8 | 2.2 | 0.5 | 1.0 | 74.4 |

TABLE II

BIODISTRIBUTION IN NORMAL MICE AFTER 120 MINUTES
(Numbers expressed as percentage of radioactive agent initially injected)

| Agent | Blood | Liver | Kidneys | Stomach | Intestine | Urine |
|---|---|---|---|---|---|---|
| Tc-99m-MAGGG | 0.03 | 0.08 | 0.06 | 0.02 | 1.2 | 98.5 |
| I-131 OIH | 0.14 | 0.11 | 0.06 | 0.98 | 0.16 | 96.0 |

Tables I and II clearly illustrate the rapid and selective removal of Tc-99m-MAGGG by the kidneys, with only trace amounts being taken up in other major organs. This is an important feature of an imaging agent so as to avoid damage to body tissues from radiation emitted by the radiolabel, and so as to minimize the amount of radiopharmaceutical required to be administered in order to obtain a suitable image.

Notably, these tables shown that Tc-99m-MAGGG is even more rapidly excreted by the kidneys than is I-131 OIH; the levels of Tc-99m-MAGGG in the urine at 10 minutes and 120 minutes were equal to 107.3 percent and 102.6 percent of corresponding levels of I-131 OIH. Because Tc-99m causes less tissue damage than does I-131, these results indicate that Tc-99m-MAGGG is significantly safer to use than is I-131.

EXAMPLE 5

Renal Uptake of Tc-99m-MAGGG in Probenicid-Treated Mice

In order to test the biodistribution of Tc-99m-MAGGG in mice having inhibited renal tubular transport, six mice were injected with a solution of probenicid at the rate of 50 milligrams of probenicid per kilogram of body weight. Ten minutes later, each mouse was injected with 0.1 milliliters of a solution containing 0.5 microcuries of Tc-99m-MAGGG and 0.2 microcuries of I-131 OIH. After an additional ten minutes, each mouse was sacrificed and various samples taken to determine biodistribution of radiolabeled material. The results of these samples are set forth in Table III.

TABLE III

BIODISTRIBUTION IN PROBENICID-TREATED MICE AFTER 10 MINUTES
(Numbers expressed as percentage of radioactive agent initially injected)

| Agent | Blood | Liver | Kidneys | Stomach | Intestine | Urine |
|---|---|---|---|---|---|---|
| Tc-99m-MAGGG | 6.0 | 5.9 | 5.4 | 0.24 | 1.6 | 64.7 |
| I-131 OIH | 7.0 | 3.7 | 3.6 | 0.75 | 2.0 | 59.2 |

Table III illustrates that kidneys having decreased function are still capable of removing Tc-99m-MAGGG to a greater degree than they are capable of removing I-131 OIH. Since I-131 is the current standard against which other radiopharmaceuticals are measured, these results indicate that Tc-99m-MAGGG is an excellent compound for use in renal function diagnostic procedures.

EXAMPLES 6 AND 7

Renal Excretion of Tc-99m-MAGGG in Humans

The renal excretion of Tc-99m-MAGGG in humans was obtained based upon experiments on normal volunteers. For purposes of comparison, tests were also conducted using I-131 OIH either immediately before or after the study using Tc-99m-MAGGG.

In Example 6, the Tc-99m-MAGGG used was prepared with stannous reduction similar to the procedure set forth in Example 2, with glucoheptonate being used as an intermediate exchange ligand. In Example 7, dithionite was used as a reducing agent instead of using stannous reduction. Both examples provided Tc-99m-MAGGG having the same major peak on a HPLC column.

In both examples, the subject was injected with a dosage containing about 15 millicuries of Tc-99m-MAGGG. The comparative tests utilizing I-131 OIH involved administration of about 300 microcuries of I-131 OIH. In both instances, imaging of the kidneys, ureters, and blood pool was conducted for a period of about 30 minutes, following which the count rate in the bladder was measured.

Thereafter, the bladder was voided, and an additional image was taken to detect the presence of residual radioactivity in order to allow determination of the percent of urine radioactivity at 30 minutes. Measurements were also taken at 3 hours. The results of these tests are set forth in Table IV.

TABLE IV (Numbers expressed as percentage of radioactive agent initially injected)

| Agent | 30 minutes | 3 hours |
|---|---|---|
| Tc-99m-MAGGG | 71.8 ± 4.2 | 98.6 ± 1.6 |
| I-131 OIH | 65.5 ± 6.3 | 93.5 ± 3.2 |

Table IV clearly demonstrates that Tc-99m-MAGGG has a high renal extraction efficiency in humans, being even better than I-131 OIH. This makes Tc-99m-MAGGG an outstanding imaging agent for use in scintigraphic urography. In contrast, the most efficiently excreted Tc-99m compound prior to the present invention (Tc-99m-$CO_2$-DADS-A) was excreted nearly 20 percent less effectively than I-131 OIH.

EXAMPLE 8

Synthesis and Renal Uptake of Tc-99m-MAGGGG

Following the general synthesis steps set forth in FIG. 1 and Examples 1 and 2 with respect to the synthesis of Tc-99m-MAGGG, the compound Tc-99m-mercaptoacetylglycylglycylglycylglycine (Tc-99m-MAGGGG) was prepared. This was accomplished utilizing glycylglycylglycylglycine in place of glycylglycylglycine in Example 1.

Tc-99m-MAGGGG was then administered to mice using a procedure similar to that described in Example 4. Biodistribution measurements were taken 10 minutes and 120 minutes after injection. The results of these measurements are shown in Table V.

TABLE V

BIODISTRIBUTION OF Tc-99m-MAGGGG
(Numbers expressed as percentage of radioactive agent initially injected)

| Time (min) | Blood | Liver | Kidneys | Stomach | Intestine | Urine |
|---|---|---|---|---|---|---|
| 10 | 2.7 | 9.9 | 3.3 | .2 | 10.3 | 58.4 |
| 120 | .04 | 1.1 | .2 | .05 | 16.0 | 82.5 |

It was calculated that the levels of Tc-99m-MAGGGG in the urine at 10 minutes and 120 minutes were equal to 86.7 percent and 87.6 percent, respectively, of the corresponding levels of I-131 OIH, indicating that this compound is a possible substitute for I-131 OIH. Increases in hepatobiliary excretion as shown by intestine radioactivity indicates decreased specificity, however.

EXAMPLE 9

Synthesis and Renal Uptake of Tc-99m-MAGG-Alanine

Following the general synthesis steps set forth in FIG. 1 and Examples 1 and 2, the compound Tc-99m-mercaptoacetylglycylglycylalanine was prepared, utilizing glycylglycylalanine in place of glycylglycylglycine in Example 1.

Tc-99m-MAGG-Alanine was then administered to mice using a procedure similar to that described in Example 4. Biodistribution measurements were taken 10 minutes and 120 minutes after injection. The results of these measurements are shown in Table VI.

TABLE VI

BIODISTRIBUTION OF Tc-99m-MAGG-Alanine
(Numbers expressed as percentage of radioactive agent initially injected)

| Time (min) | Blood | Liver | Kidneys | Stomach | Intestine | Urine |
|---|---|---|---|---|---|---|
| 10 | 2.6 | 2.6 | 5.2 | .2 | 1.6 | 75.1 |
| 120 | .2 | .1 | .3 | .2 | 2.2 | 96.0 |

The levels of Tc-99m-MAGG-Alanine in the urine at 10 minutes and 120 minutes were equal to 106.4 percent and 102.2 percent, respectively, of the corresponding levels of I-131 OIH, indicating that this compound would be an excellent choice for use in scintigraphic urography procedures in place of I-131 OIH.

EXAMPLE 10

Synthesis and Renal Uptake of Tc-99m-MAGG-Aspartic Acid

Following the general synthesis steps set forth in FIG. 1 and Examples 1 and 2, the compound Tc-99m-mercaptoacetylglycylglycylaspartic acid was prepared, utilizing glycylglycylaspartic acid in place of glycylglycylglycine in Example 1.

Tc-99m-MAGG-Aspartic Acid was then administered to mice using a procedure similar to that described in Example 4. Biodistribution measurements are shown in Table VII.

TABLE VII

BIODISTRIBUTION OF Tc-99m-MAGG-Aspartic Acid
(Numbers expressed as percentage of radioactive agent initially injected)

| Time (min) | Blood | Liver | Kidneys | Stomach | Intestines | Urine |
|---|---|---|---|---|---|---|
| 10 | 6.6 | 6.51 | 4.7 | .4 | 2.7 | 50.1 |
| 120 | .3 | 1.5 | .2 | .3 | 6.2 | 87.4 |

The levels of Tc-99m-MAGG-Aspartic Acid in the urine at 10 minutes and 120 minutes were equal to 64.2 percent and 94.1 percent, respectively, of the corresponding levels of I-131 OIH. The low clearance at 10 minutes makes the suitability of this compound as a substitute for I-131 OIH questionable.

EXAMPLE 11

Synthesis and Renal Uptake of Tc-99m-MAGG-Glutamine

The compound Tc-99m-MAGG-Glutamine was prepared following the general synthesis steps set forth in FIG. 1 and Examples 1 and 2, except that glycylglycylglutamine was used in place of glycylglycylglycine in Example 1.

Tc-99m-MAGG-Glutamine was then administered to mice using a procedure similar to that described in Example 4. Biodistribution measurements are shown in Table VIII.

TABLE VIII

BIODISTRIBUTION OF Tc-99m-MAGG-Glutamine
(Numbers expressed as percentage of radioactive agent initially injected)

| Time (min) | Blood | Liver | Kidneys | Stomach | Intestines | Urine |
|---|---|---|---|---|---|---|
| 10 | 3.2 | 4.5 | 4.2 | .2 | .9 | 70.7 |
| 120 | .04 | .8 | .1 | .04 | 1.0 | 95.9 |

The levels of Tc-99M-MAGG-Glutamine in the urine at 10 minutes and 120 minutes were equal to 97.6 percent and 103.4 percent, respectively, of corresponding levels of I-131 OIH, indicating that this compound is an excellent substitute for I-131 OIH for use in scintigraphic urography procedures.

EXAMPLE 12

Synthesis and Renal Uptake of Tc-99m-MAGG-Phenylalanine

The compound Tc-99m-MAGG-Phenylalanine was prepared following the general synthesis steps set forth in FIG. 1 and Examples 1 and 2, except that glycylglycylphenylalanine was used in place of glycylglycylglycine in Example 1.

Tc-99m-MAGG-phenylalanine exists in two separable diasteriomeric forms, identified by the labels -A and -B. The diasteriomeric forms Tc-99m-MAGG-Phenylalanine-A and Tc-99m-MAGG-Phenylalanine-B were separated and separately administered to mice using a procedure similar to that described in Example 4. Biodistribution measurements for these two compounds are shown in Tables IX and X, respectively.

TABLE IX

BIODISTRIBUTION OF Tc-99m-MAGG-Phenylalanine-A
(Numbers expressed as percentage of
radioactive agent initially injected)

| Time (min) | Blood | Liver | Kidneys | Stomach | Intestines | Urine |
|---|---|---|---|---|---|---|
| 10 | 9.7 | 22.16 | 7.6 | .4 | 7.7 | 32.3 |
| 120 | .2 | 2.3 | .2 | .3 | 26.1 | 69.5 |

TABLE X

BIODISTRIBUTION OF Tc-99m-MAGG-Phenylalanine-B
(Numbers expressed as percentage of
radioactive agent initially injected)

| Time (min) | Blood | Liver | Kidneys | Stomach | Intestines | Urine |
|---|---|---|---|---|---|---|
| 10 | 19.4 | 14.7 | 5.3 | 1.0 | 14.9 | 16.2 |
| 120 | .8 | 3.0 | .4 | .9 | 41.7 | 48.6 |

The levels of Tc-99m-MAGG-Phenylalanine-A in the urine at 10 minutes and 120 minutes were equal to 43.9 percent and 73.5 percent, respectively, of corresponding levels of I-131 OIH. The levels of Tc-99m-MAGG-Phenylalanine-B in the urine at 10 minutes and 120 minutes were equal to 22.0 percent and 52.3 percent, respectively, of corresponding levels of I-131 OIH. These low percentages, taken together with the biodistribution measurements indicate that significant quantities of these compounds are taken up in various tissues, indicate that Tc-99m-MAGG-Phenylalanine is not well-suited for routine use in typical scintigraphic urography procedures.

EXAMPLE 13

Synthesis and Renal Uptake of
Tc-99m-MAGG-Asparagine

The compound Tc-99m-MAGG-Asparagine was prepared following the general synthesis steps set forth in FIG. 1 and Examples 1 and 2, except that glycylglycylasparagine was used in place of glycylglycylglycine in Example 1.

Tc-99m-MAGG-Asparagine exists in two separable diasteriomeric forms, identified by the labels -A and -B. The diasteriomeric forms Tc-99m-MAGG-Asparagine-A and Tc-99m-MAGG-Asparagine-B were separated and each administered to mice using a procedure similar to that described in Example 4. Biodistribution measurements for these two compounds are shown in Tables XI and XII, respectively.

TABLE XI

BIODISTRIBUTION OF TC-99m-MAGG-Asparagine-A
(Numbers expressed as percentage of
radioactive agent initially injected)

| Time (min) | Blood | Liver | Kidneys | Stomach | Intestines | Urine |
|---|---|---|---|---|---|---|
| 10 | 2.6 | 5.3 | 4.1 | .2 | .9 | 74.1 |
| 120 | 0.04 | .6 | 0.04 | .2 | 2.2 | 94.5 |

TABLE XII

BIODISTRIBUTION OF Tc-99m-MAGG-Asparagine-B
(Numbers expressed as percentage of
radioactive agent initially injected)

| Time (min) | Blood | Liver | Kidneys | Stomach | Intestines | Urine |
|---|---|---|---|---|---|---|
| 10 | 2.6 | 6.3 | 4.2 | .1 | .9 | 73.6 |
| 120 | 0.03 | .4 | 0.04 | .02 | 1.8 | 96.7 |

The levels of Tc-99m-MAGG-Asparagine-A in the urine at 10 minutes and 120 minutes were equal to 98.9 percent and 102.2 percent, respectively, of corresponding levels of I-131 OIH. The levels of Tc-99m-MAGG-Asparagine-B in the urine at 10 minutes and 120 minutes were equal to 97.1 percent and 103.5 percent, respectively, of corresponding levels of I-131 OIH.

These high percentages indicate that either diasteriomeric form of Tc-99m-MAGG-Asparagine would be suitable as a replacement for I-131 OIH in scintigraphic urography procedures. Further, since both diasteriomeric forms are suitable replacements for I-131 OIH, there is no need to separate the diasteriomeric forms from one another, making the use of this compound in a kit form entirely practical.

EXAMPLE 14

Synthesis and Renal Uptake of
Tc-99m-MAGG-Glutaric Acid

Following the generally synthesis steps set forth in FIG. 1 and Example 1 and 2, the compound Tc-99m-MAGG-Glutaric Acid was prepared following, except that glycylglycylglutaric acid was used in place of glycylglycylglycine in Example 1.

Tc-99m-MAGG-Glutaric Acid exists in two separable diasteriomeric forms, identified by the labels -A and -B. These diasteriomeric forms were separated and each administered to mice using a procedure similar to that described in Example 4. Biodistribution measurements for these compounds are shown in Tables XIII and XIV, respectively.

TABLE XIII

BIODISTRIBUTION OF Tc-99m-MAGG-Glutaric Acid-A
(Numbers expressed as percentage of
radioactive agent initially injected)

| Time (min) | Blood | Liver | Kidneys | Stomach | Intestines | Urine |
|---|---|---|---|---|---|---|
| 10 | 7.5 | 4.8 | 5.2 | .4 | 1.8 | 50.2 |
| 120 | .2 | 1.7 | .1 | .2 | 1.1 | 94.2 |

TABLE XIV

BIODISTRIBUTION OF Tc-99m-MAGG-Glutaric Acid-B
(Numbers expressed as percentage of
radioactive agent initially injected)

| Time (min) | Blood | Liver | Kidneys | Stomach | Intestines | Urine |
|---|---|---|---|---|---|---|
| 10 | 4.2 | 3.6 | 6.5 | .2 | 1.1 | 65.1 |
| 120 | .2 | .9 | .1 | .4 | 2.4 | 94.3 |

The levels of Tc-99m-MAGG-Glutaric Acid-A in the urine at 10 minutes and 120 minutes were equal to 73.0 percent and 99.8 percent, respectively, of corresponding levels of I-131 OIH. The levels of Tc-99m-MAGG-Glutaric Acid-B in the urine at 10 minutes and 120 minutes were equal to 88.6 percent and 98.8 percent, respectively, of corresponding levels of I-131 OIH. These findings indicate that this compound might be considered as a substitute for I-131 OIH.

EXAMPLE 15

Synthesis of Other Tc-99m $N_3S$ System Compounds

Following the generally synthesis steps set forth in FIG. 1 and in Examples 1 and 2 with respect to the synthesis of Tc-99m-MAGGG, other Tc-99m compounds incorporating the $N_3S$ system within the scope of the present invention are synthesized. For instance, with respect to the following general formula:

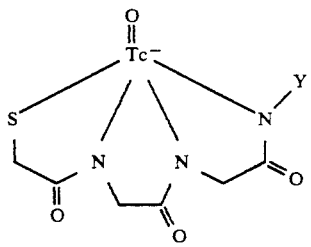

one such Tc-99m compound is synthesized wherein Y is —CH$_2$CH$_2$CO$_2$H. This compound is prepared by utilizing NH$_2$CH$_2$CONHCH$_2$CONHCH$_2$CH$_2$CO$_2$H in place of glycylglycylglycine in Example 1.

Based upon the results of tests with Tc-99m-MAGGG, it is to be expected that this compound will exhibit a significant extraction efficiency.

EXAMPLE 16

Another Tc-99m compound having the genera formula set forth in Example 15, but where Y is —CH(CH$_2$CH$_3$)CO$_2$H, is synthesized following the general synthesis steps set forth in FIG. 1 and Examples 1 and 2, but where the starting ligand is NH$_2$CH$_2$CONHCH$_2$CONHCH(CH$_2$CH$_3$)CO$_2$H.

Based upon the results of tests with Tc-99m-MAGGG, it is to be expected that this compound will exhibit a significant renal extraction efficiency.

EXAMPLE 17

Another Tc-99m compound having the genera formula set forth in Example 15, but where Y is —CH$_2$CONH$_2$, is synthesized following the general synthesis steps set forth in FIG. 1 and Examples 1 and 2, but where the starting ligand is NH$_2$CH$_2$CONHCH$_2$CONHCH$_2$CONH$_2$.

Based upon the results of tests with Tc-99m-MAGGG, it is to be expected that this compound will exhibit a significant renal extraction efficiency.

EXAMPLE 18

Synthesis of Tc-99m Compounds Having an N$_4$ System

In addition to those Tc-99m compounds synthesized above having an N$_3$S ring system, it is also possible to synthesize related Tc-99m compounds incorporating an N$_4$ System. For example, with respect to the following general formula:

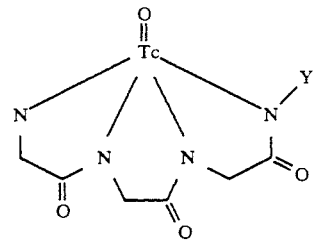

a novel Tc-99m compound, where Y is —CH$_2$CO$_2$H, was synthesized utilizing the general synthesis steps set forth in FIG. 1 and Example 2, but where the ligand NH$_2$CH$_2$CONHCH$_2$CONHCH$_2$CONHCH$_2$CO$_2$H (glycylglycylglycylglycine) was reacted with sodium pertechnetate.

The resulting compound, Tc-99m-GGGG, was administered to mice using a procedure similar to that described in Example 4. Biodistribution measurements taken 10 minutes and 120 minutes after injection are shown in Table XV.

TABLE XV

| | BIODISTRIBUTION OF Tc-99m-GGGG (Numbers expressed as percentage of radioactive agent initially injected) | | | | | |
|---|---|---|---|---|---|---|
| Time (min) | Blood | Liver | Kidneys | Stomach | Intestines | Urine |
| 10 | 3.8 | 3.4 | 4.2 | 1.1 | 2.2 | 69.3 |
| 120 | .5 | 1.0 | 1.1 | 1.9 | 2.5 | 90.0 |

The levels of Tc-99m-GGGG in the urine at ten minutes and at 120 minutes were equal to 89.4 percent and 96.7 percent respectively, of corresponding levels of I-131 OIH, indicating that this compound is a possible substitute for I-131 OIH.

EXAMPLE 19

It is also possible to prepare other Tc-99m compounds involving some structural changes in the ring system. For example, it is expected that the following general class of compounds will also exhibit significant renal extraction efficiencies:

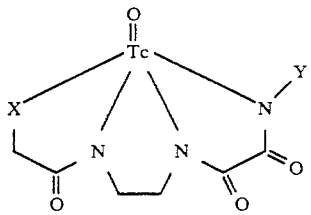

For example, by starting with NH$_2$CH$_2$CH$_2$NHCOCONHCH$_2$CO$_2$H and following the general synthesis steps of FIG. 1 and Examples 1 and 2, the compound having the general formula above is synthesized, where X is S, and Y is —CH$_2$CO$_2$H.

EXAMPLE 20

Another Tc-99m compound having the general formula set forth below:

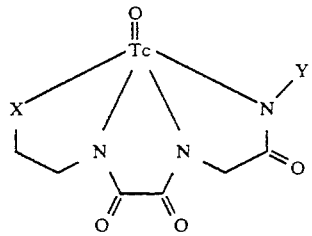

where X is S, and Y is —CHCH$_3$CO$_2$H, is synthesized following the general synthesis steps of FIG. 1 and Example 2 by reacting C$_6$H$_5$COSCH$_2$CH$_2$NH-COCONHCH$_2$CONHCHCH$_3$CO$_2$H with sodium pertechnetate.

Based upon the results of the tests done with Tc-99m-MAGGG, it is to be expected that this compound will exhibit a significant renal extraction efficiency.

EXAMPLE 21

Another Tc-99m compound having the general formula:

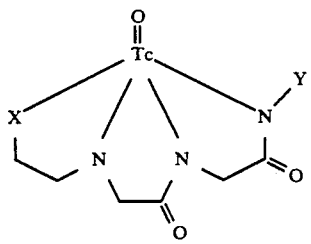

where X is S, and Y is —CH$_2$CH$_2$CO$_2$H, is synthesized following the generally synthesis steps of FIG. 1 and Example 2 by reacting CH$_3$COSCH$_2$CH$_2$NHCH$_2$CONHCH$_2$CONHCH$_2$CH$_2$CO$_2$H with sodium pertechnetate.

Based upon the results of the tests done with Tc-99m-MAGGG, it is to be expected that this compound will exhibit a significant renal extraction efficiency.

EXAMPLE 22

Another Tc-99m compound having the general formula:

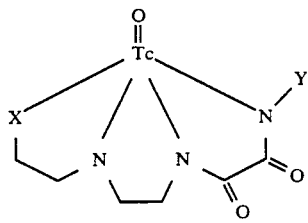

where X is N, and Y is —CH$_2$CO$_2$H is synthesized following the general synthesis steps of FIG. 1 and Example 2 by reacting H$_2$NCH$_2$CH$_2$NHCH$_2$CH$_2$NHCOCONHCH$_2$CO$_2$H with sodium pertechnetate.

Based upon the results of the tests done with Tc-99m-MAGGG, it is to be expected that this compound will exhibit a significant renal extraction efficiency.

From the foregoing, it will be appreciated that the novel Tc-99m compounds of the present invention will be useful as imaging agents in scintigraphic urography procedures because of their substantial renal extraction efficiencies and their substantial avoidance of adverse properties such as isomerism. Additionally, the ability to provide the precursors to these Tc-99m compounds in kit form requiring nothing more than a mixing and heating step makes the use of Tc-99m as a radiolabel extremely practical.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by U.S. Letters Patent is:

1. A ligand capable of reacting with a suitable Tc-99m-pertechnetate salt to form a Tc-99m chelate, said ligand having the general formula:

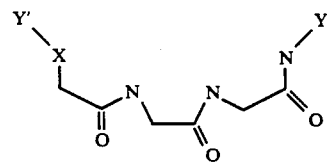

where X is S; Y' is a protective group which protects the sulfur from oxidation; and Y is —H$_2$ or Y is:

and where R$_1$ is —H, —CH$_3$, or —CH$_2$CH$_3$; R$_2$ is —H, —CH$_2$CO$_2$H, —CH$_2$CONH$_2$, —CH$_2$CH$_2$CO$_2$H, —CH$_2$CH$_2$CONH$_2$, —CH$_3$, —CH$_2$CH$_3$, —CH$_2$C$_6$H$_5$, or —OCH$_2$OH; and Z is —H, —CO$_2$H, —CONH$_2$, —SO$_3$H, —SO$_2$NH$_2$, or —CONHCH$_2$CO$_2$H.

2. A ligand as defined in claim 1, wherein the protective group is —COCH$_3$, —COC$_6$H$_5$, —CH$_2$NHCOCH$_3$, or —COCH$_2$OH.

3. A ligand as defined in claim 1, where Y' is —COC$_6$H$_5$, and Y is —CH$_2$CO$_2$H.

4. A ligand as defined in claim 1, wherein Y is —CH(CH$_3$)CO$_2$H; —CH(CH$_2$CONH$_2$)CO$_2$H; or —CH(CH$_2$CH$_2$CONH$_2$)COOH.

5. A ligand capable of reacting with a suitable Tc-99m-pertechnetate salt to form a Tc-99m chelate, said ligand having the general formula:

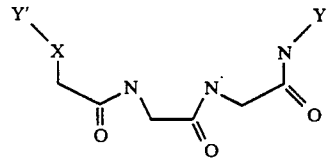

where X is N; Y' is —H$_2$; and Y is:

and wherein R$_1$ and R$_2$ are —H and Z is —H.

6. A ligand capable of reacting with a suitable Tc-99m-pertechnetate salt to form a Tc-99m chelate, said ligand having the general formula:

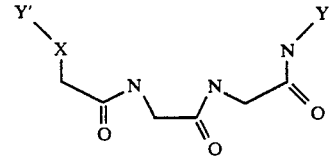

where X is N; Y' is —H$_2$; and Y is:

7. A ligand capable of reacting with a suitable Tc-99m-pertechnetate salt to form a Tc-99m chelate, said ligand having the general formula:
and wherein $R_1$ and $R_2$ are —H and Z is —SO$_3$H.
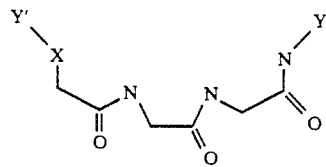
where X is N; Y' is —H$_2$; and Y is:
and wherein $R_1$ and $R_2$ are —H and Z is —SO$_2$NH$_2$.
* * * * *

UNITED STATES PATENT AND TRADEMARK OFFICE
CERTIFICATE OF CORRECTION

PATENT NO. : 5,322,929
DATED : June 21,1994
INVENTOR(S) : ALAN FRITZBERG et al.

It is certified that error appears in the above-indentified patent and that said Letters Patent is hereby corrected as shown below:

```
Column 9, line 48, "contexts" should be --context--
Column 9, line 60, "fleshly" should be --freshly--
Column 10, line 54, "size mice" should be --six mice--
Column 16, line 22, "Example" should be --Examples--
Column 16, line 23, delete "following"
Column 17, line 24, "genera" should be --general--
Column 17, line 35, "genera" should be --general--
```

Signed and Sealed this

Eighth Day of November, 1994

Attest:

BRUCE LEHMAN

*Attesting Officer*  *Commissioner of Patents and Trademarks*